Figure 1:
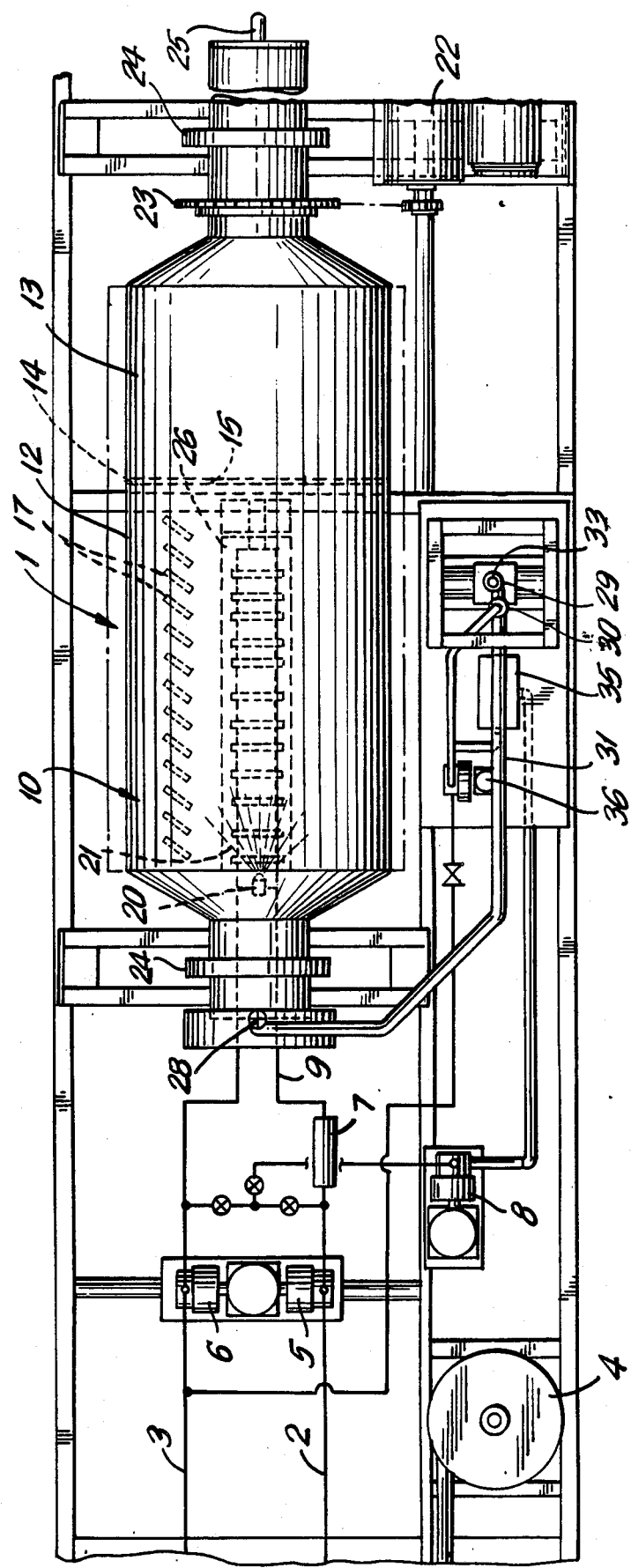

United States Patent [19]

Miller et al.

[11] Patent Number: 4,681,710
[45] Date of Patent: Jul. 21, 1987

[54] PRODUCTION OF SULFONATED AMINES

[75] Inventors: Ralph Miller, Pleasantville, N.Y.; Jakob L. Bollini; Robert Schneider, both of Greensboro, N.C.

[73] Assignee: Ciba-Geigy Corporation, Ardsley, N.Y.

[21] Appl. No.: 714,769

[22] Filed: Mar. 22, 1985

[51] Int. Cl.⁴ .......................................... C07C 143/58
[52] U.S. Cl. ..................................... 260/508; 260/509
[58] Field of Search ............................... 260/508, 509

[56] References Cited

U.S. PATENT DOCUMENTS 4,435,336  3/1984  Emde et al. .......................... 260/508

OTHER PUBLICATIONS

Hall et al., C.A., 80, 82400u (1974).
Boehm et al., C.A., 77, 19379s (1972).
Kisel'nikov et al., C.A., 53, 4216d (1959).
Fiat Final Report No. 1313, 1948.

*Primary Examiner*—Nicky Chan
*Attorney, Agent, or Firm*—Karl F. Jorda

[57] ABSTRACT

A process for the preparation of sulfonated aromatic amines starting with the corresponding aromatic amine sulfate salt which employs a rotating reactor in which there is maintained a rapidly moving heated cascading bed of solid particles composed largely of the final product whose temperature is above or brought above the rearrangement temperature. The reactants are fed to the bed at such a rate that the cascading movement of the bed is unaffected. The heat imparted to the amino hydrogen sulfate within the bed by the surrounding particles orient the desired rearrangement to take place along with the vaporization and elimination of water.

10 Claims, 2 Drawing Figures

PRODUCTION OF SULFONATED AMINES

FIELD OF INVENTION

This invention relates to the economic production of sulfonated aromatic amines and more particularly to the direct production of such amines, in the absence of solvent reaction media.

BACKGROUND OF THE INVENTION

The more commonly used and thus economically important sulfonated amines are those derived from aniline, the toluidines, xylidines, chloroanilines, napthylamines, aminoanthraquinones and the like. The simplest of the sulfonated aromatic amines is sulfanilic acid of the formula:

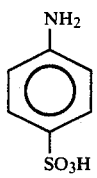

(1)

Millions of pounds of sulfanilic acid are consumed annually, primarily to produce dyestuffs but some is also used in the synthesis of other materials including substantial amount of phenylhydrazine-p-sulfonic acid. The major portion of the sulfanilic acid is consumed in the manufacture of fluorescent whitening agents. Such fluorescent dyestuffs are applied to paper, woven and non-woven textiles, and are components of soap and detergent laundering agents. Such fluorescent whitening agents are marketed under the Tinopal trademark. For example, in excess of a million pounds a year is used for the manufacture of one of the whiteners applied to paper. Thus, any savings effected in the production of sulfanilic acid are of major economic interest.

The most straight forward synthesis of these amines and particularly sulfanilic acid consists of reacting the amine, aniline, with sulfuric acid in substantially stoichiometric proportions to form aniline hydrogen sulfate (AHS), followed by splitting off water and the migration rearrangement of the resulting sulfonic acid group to the para position according to the following equations:

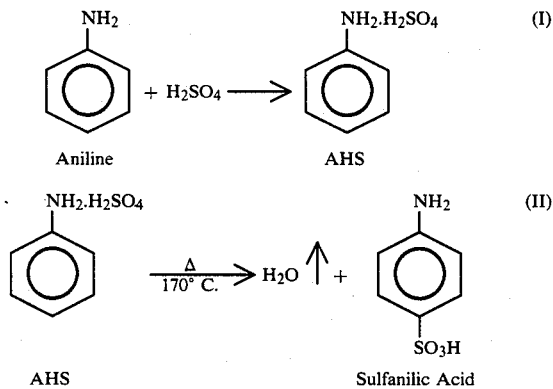

These reactions have been carried out directly or in the presence of inert, high boiling, water-immiscible solvents (Jabobs: *Ind. Eng. Chem.* 35; pg. 321-323). The syntheses using solvents produce a product of better appearance (Gardner color <9) but solvent cost, handling, removal and recycling impose excessive costs that are not competitively bearable. Thus most sulfanilic acid is now prepared in the absence of solvents.

The reaction (I) between aniline and sulfuric acid to form the aniline hydrogen sulfate proceeds as rapidly as the reactants are mixed and is exothermic. The heat of the exothermic reaction causes the temperature of the reaction mass to rise. Aniline hydrogen sulfate melts at about 160° C. It is very soluble in water at elevated temperatures. The temperature at which it liquefies varies with the amount of water in the mixture.

To cause water to be split off and to promote the para-rearrangement of reaction (II) at a slow but measurable rate, the minimum temperature must be about 165° C. At this temperature the aniline hydrogen sulfate is slowly converted, by an endothermic reaction, to sulfanilic acid. Sulfanilic acid, (in contrast to the aniline hydrogen sulfate salt), is stable and does not melt up to its decomposition temperature which is about 280° C.

It is instructive to visually observe the conversion to sulfanilic acid of a molten mass of aniline hydrogen sulfate. As stated above, when water is present in the aniline hydrogen sulfate, the mixture forms a liquid or pasty mass at temperatures below 160° C. As the mass is heated, water is driven off so that substantially none is present at about 160° C. When the temperature is raised to the rearrangement temperature, the conversion starts. Sulfanilic acid is insoluble in molten aniline hydrogen sulfate. During the early stages of the conversion the molten mass becomes a pasty, sticky mass of a liquid phase and a dispersed solid phase. Bubbles form in the liquid from the water vapor that evolves. As the conversion continues, the mass becomes increasingly solid with a liquid phase dispersed within it. The upper surface is no longer smooth. It assumes a pockmarked appearance from the simultaneous escape of water vapor and the solidification of that part of the mixture from which it has emerged.

By maintaining the sample above the conversion temperature for a sufficient period of time, the sample is substantially completely converted to a block of solid sulfanilic acid which strongly adheres to the surface with which it was in contact during the conversion. It is this behavior pattern of the mixture during its conversion that has led to previously employed processes briefly described below.

During this period of rearrangement and water elimination, color bodies of indeterminate composition form; causing a grayish or deep purplish product. For many uses this product, if not too intensely colored, can be used without further upgrading. It is known that iron tends to catalyze a reaction which also forms color bodies in the product.

The classical process for making sulfanilic acid is the "baking" process wherein aniline acid and sulfuric acid are mixed together to form the solid aniline hydrogen sulfate salt (Fiat Report 1313) (1945). In one variant, a batch-type process, a layer of the solid salt several centimeters thick is spread on lead or iron trays. The loaded trays are then slowly passed through an oven or tunnel kiln and heated to above the rearrangement and water elimination temperature. The eliminated water is vented from the kiln and condensed together with any vaporized aniline. When the trays emerge, conversion to sulfanilic acid is substantially complete, the trays are emptied and the cycle is repeated by reloading the trays with additional aniline hydrogen sulfate.

The molten aniline hydrogen sulfate, prior to rearrangement and water elimination is corrosive, especially to iron. In the trays, while corrosion takes place, the rate of corrosion and erosion of metal is not excessive because an adherent retarding surface coating of sulfanilic acid forms on the surface of the trays. This coating also retards migration of the colored corrosion products through the rearranging mass.

A variant of the tray "baking" process employs an elongated, rotating cylindrical steel reactor with an opening and cover plate in its center. The interior is tapered slightly so that non-sticky solids will flow towards the center opening. Flanges are attached to both ends. By means of the flanges, articulated end pieces with center holes are connected to the reactor. Hollow shafts, having openings coinciding with the center holes are attached to the end pieces. By appropriate valves the hollow shafts are used to charge liquid aniline and sulfuric acid into the reactor at one end and to vent the water vapor at the other end. By suitable gearing, the shafts and reactor are rotated. Heavy rods or steel balls or both, are placed within the reactor so that the rotating reactor behaves as product-comminuting ball or rod mill. The reactor is mounted within a furnace which supplies the heat necessary for the rearrangement reaction II and to drive off the water vapor.

Aniline and sulfuric acid, in substantailly equimolar amounts are charged to the rotating reactor to form aniline hydrogen sulfate therein. When the charging is completed, the temperature within the furnace is raised to heat the reactor and its contents above the rearrangement temperature. The released water is vented through one of the hollow shafts exiting the end of reactor. The water is externally condensed.

It is possible to follow the progress of the rearrangement and to observe its completion by following the rate and amount of water being condensed. Another, more empiric indication of the progress of the reactions is the sound emanating from the equipment. At the beginning of the reaction between the aniline and the sulfuric acid, the thudding sound of the rods dropping during the rotation can be heard. As the aniline hydrogen sulfate mass is heated and the conversion starts to take place the mixture becomes a pasty, sticky mass. The impact of the falling rods is absorbed by the pasty mass, which causes a decided dulling of the noise. As the reaction mixture appreciably converts to sulfanilic acid and becomes an increasingly dry solid mass, the character of the noise slowly reverts to the sharper impact sounds. The ultimate test indicating that the conversion to sulfanilic acid is substantially complete is the cessation of water condensation. As soon as water stops coming over, heating is stopped and the reactor is allowed to cool. The rotation of the reactor is continued for a sufficient period to break away the sulfanilic acid scale from the reactor's interior surface and to break up any large lumps. The rotation is then stopped, the cover plate in the center is removed and the product discharged from the center opening.

The rod mill reactor and the tunnel kiln process are both basically batch processes. The reactor has to be heated and then cooled. Heat transfer is poor during the period when the reaction mixture is pasty and scale is adhering to the walls. The rod mill reactor must also serve as a mill to break up the lumps and break off the scale, thereby prolonging the production cycle.

Other non-solvent processes include forming a pool of molten aniline hydrogen sulfate in which a segment of a continuously rotating drum dryer is immersed. The interior of the dryer is heated by high pressure steam or some other heat transfer fluid. The aniline hydrogen sulfate adhering to the exterior surface of the drum, after it emerges from the pool, is heated above the rearrangement temperature. The speed of rotation of the drum and the temperature to which the adherent film is raised are correlated so that rearrangement to sulfanilic acid is complete before reentry of the coated portion into the molten pool. A doctor blade is positioned so that the completely rearranged sulfanilic acid is scraped off and collected before the drum reenters the molten pool. While feasible, the parameters of temperature, rotation rate, product adherence, etc., render production control difficult so that this process is not economically viable.

Another method is based on mixing sulfuric acid, aniline and a small amount of water at about 125°–145° C. and spraying the resulting solution into a spray dryer along with air heated to about 400° C. The temperature of the outgoing air is held at about 260°–270° C. The resulting air stream in which solid sulfanilic acid particles are entrained is passed through a cyclone and bag filters. This separates the air from the solids. This method requires completion of the rearrangement in a very short period—in the order of a second. Current environmental requirements are very stringent and to meet even minimal solid separation requirements of the solid product from the gases necessitates inordinately expensive arrangements and investments.

Another variant involves utliization of fluidized bed technology wherein either solid or molten aniline hydrogen sulfate is continuously fed to a fluidized bed of sulfanilic acid. The bed is fluidized by a sufficiently hot inert gas to maintain the bed above the rearrangement temperature. The water vapor, which evolves, leaves with the vented inert fluidizing gas. Sulfanilic acid is continuously or periodically withdrawn from the reaction bed. The inert gas, which may be heated air at about 200° C.–250° C. is not only used as the fluidizing medium but also as the heating element and the carrier for sweeping out the water. Of course, this method requires very efficient cyclones and/or bag filters and often porous metal filters fitted with cyclic filter cleansing means to remove the product from the vented gases. These are expensive so that this method is non-competitive with the batch rod mill method.

THE INVENTION

It is an object of this invention to produce sulfonated aromatic amines of the formula

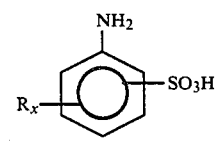

where R is H, CH$_3$, C$_2$H$_5$ or halogen and x is the integer 0 to 2, from a designated aromatic amine of the formula

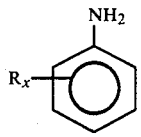

where R and x have the meanings given above and sulfuric acid by a continuous process, employing simple equipment, and operated in a manner whereby the reactor walls are rarely if ever contacted by the liquid portion of the reaction mixture when such mixture is in its sticky adherent, corrosive state.

A further object of this invention is to prepare a sulfonated amine without the need for forming the precursor solid amine sulfate salt as an initial processing step and wherein a substantial amount of the heat of reaction between the amine and sulfuric acid is usefully employed.

An additional objective of this invention is to raise the temperature of a mixture containing a sulfonated aromatic amine and its precursor sulfate salt above its rearrangement temperature by heat transfer under very much better conditions than has been employed or previously described.

The process of this invention in its broadest aspect is based upon establishing, at a temperature above the required rearrangement temperature, a rolling, cascading bed of solid particles of the desired sulfonated amine in a heated, rotating reactor and spraying into the vortex of the moving cascade particles of either the liquid precursor amino-hydrogen sulfate or sulfuric acid and the appropriate amine. The spray rate and pattern are each controlled so that the liquid is distributed in a very thin film over a very large surface area of the particles within the vortex. While maintaining this condition, only a small fraction of the particles within the moving bed are wetted by the liquid feed. Because of the presence of a very large number of particles which are dry or have not been appreciably wetted compared with the number of wetted particles, the surface wetted particles, are immediately impacted by dry particles. Consequently, the wetted surface is exposed so briefly that there is no tendency for the formation of agglomerates in that fraction of the bed contacted by the liquid feed. This also reduces or eliminates any appreciable contacting of the reactor walls by the liquid feed.

Because of its overwhelming economic importance, the application of the invention to sulfanilic acid is stressed. In one aspect, concentrated sulfuric acid and liquid aniline are each sprayed in a mist-like pattern into the vortex of a cascading heated bed of sulfanilic acid particles formed within the rotating heated reactor. The spray patterns are so directed that they intersect, and interact with each other just prior to entering the bed so that the particles are wetted by liquid aniline hydrogen sulfate formed essentially in situ.

In another aspect of the invention, a spray nozzle is installed above a cascading bed of hot sulfanilic acid particles. Immediately preceding the spray nozzle is a mixing chamber connected to two feed lines. Stoichiometric amounts of aniline and sulfuric acid are fed to the mixing chamber. High temperature molten aniline hydrogen sulfate is formed in the mixing chamber and finely divided droplets are sprayed into the vortex of the cascading bed.

A preferred method of heating the fluidized, rotating reaction medium and introduced reactants is by induction heating. A water-cooled induction heating strip is positioned beneath and along substantially at least the introductory and initial bed portions of the reactor, preferably along substantially most of the reactor feed zone. This arrangement provides maximum bed input to the reaction along that part of the inside of the reactor adjacent to and passing over the induction strip. This arrangement has the advantage or rapidly responsive temperature control as there is rapid heat transfer via the indicator without the lagging response caused by heat sinks. The induction is not hot and thus provides no heat sink to slow thermal responses.

To control the temperature of the emerging aniline hydrogen sulfate feed, water can be blended with the aniline feed. Although some of the heat of reaction is taken up by vaporizing this added water, the overall spray pattern is more easily controlled thereby simplifying the overall process.

It has been emphasized that an essential requirement of this invention is that the amount of amino hydrogen sulfate in the cascading bed of particles of final product be such that the cascading bed always remains free flowing and that there be little or no contact between the heated interior surface of the reactor and sticky particles. The quantity of potentially sticky particles that can be present in the bed without causing the sticky particles to adhere to the interior surface or the formation of a bed which does not cascade readily depends upon the equipment in which the process is carried out. To obtain a measure of the quantity of sticky material which can be present without causing either of the above undesirable effects, the following tests were carried out.

Figure 2:
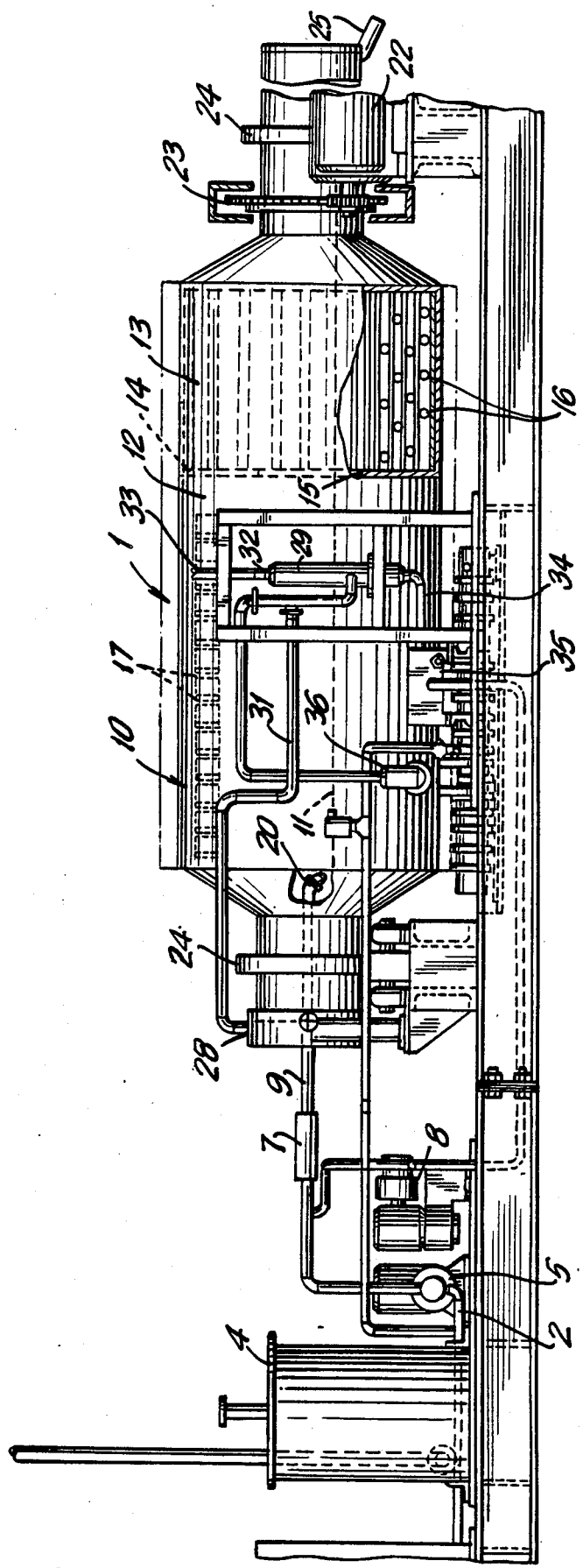

FIGS. 1 and 2 show an industrial scale sulfanilic acid production unit in a top and side elevation view, respectively. The figures are described in detail in Examples 4 and 5.

EXAMPLE 1

FIGS. 1 and 2 show an industrial scale sulfanilic acid production unit in a top and side elevation view, respectively. The figures are described in detail in Examples 4 and 5.

A 500 ml. rotovac, glass flask connected to a condenser was filled with 100 grams of a powdered mixture containing 5 grams of aniline hydrogen sulfate and 95 grams of sulfanilic acid. The flask was immersed in an oil bath whose temperature was about 160° C. The flask was rotated clockwise at a rate so that the powder was carried upward to about the seven o'clock position before the uppermost layer of powder slid downwards. The rate was such that the falling powder did *not* give the appearance of cascading. While the flask was continuously rotating, the temperature of the oil bath was slowly raised to about 210° C. As the heating continued, water vapor was evolved and condensed. After several hours water stopped coming over. The oil bath was lowered and the flask and its contents allowed to cool. The product was analyzed. It was found that more than 98% of the aniline hydrogen sulfate had been converted to sulfanilic acid.

At no time during this procedure was there any change in the behavior of the bed. There was no evidence of any sticking of the powder to the surface of the glass. By proceeding in this way the test material was caused to move about in the most gentle way that could be devised short of keeping it completely static.

When the above test was repeated, using a mixture containing 10 grams of aniline hydrogen sulfate and 90 grams of sulfanilic acid, there was definite evidence of material adhering to the glass surface and agglomerating of the bed.

From the foregoing it was concluded that by controlling the total amount of liquid material phase in a moving bed of powder composed largely of sulfanilic acid powder, the bed would remain free-moving providing that the fraction of liquid phase in the bed at any time was small.

EXAMPLE 2

The above test showed that the inventive concept was technically feasible. The next test was run in an available stainless steel pilot-sized test kiln 6½ inches in diameter and 11 feet long. The kiln sloped slightly downwards from the feed end to the outlet. This kiln was equipped with rotating seals. A screw feeder was connected to one end of the kiln with the other end connected to an outlet breeching. An upper opening in the outlet breeching was connected to an induced draft fan. This made it possible to pass a slight current of air through the kiln and thereby remove any vapors evolved in the kiln. A bottom outlet in the breeching was connected to a rotary valve. An opening in the seal wall of the breeching in line with kiln's outlet was equipped with a movable cover plate. The cover plate could be rotated so that it was possible to see through the opening and the entire interior of the kiln.

Six feet of the kiln was encased in a shroud containing a series of propane gas burners. Four thermocouples were installed within the shroud at about one foot intervals immediately adjacent to the kiln's outside wall. When the propane burners were on, the kiln was heated by the hot gas. The thermocouples measured the temperature within the shroud immediately adjacent to the kiln's outside wall. From previous test work it had been established that the temperature of the material within the kiln was between 35° C. and 60° C. below the temperature measured by the thermocouples. The temperature of the inside kiln wall was within a few degrees of the measured temperature.

The initial test was made using a powdered feed mixture containing about 5% aniline hydrogen sulfate and 95% sulfanilic acid. The feed rate of the mixture was set at thirty (30) pounds per hour. The speed of rotation and the inclination of the kiln was such that the solid feed occupied about 10% of the volume within the kiln. This is a normal condition when operating in the described manner. In this first test the shroud temperature was maintained between about 205° C. and 235° C.

The kiln was rotated counter-clockwise at 3 RPM. This is a linear velocity of about five (5) feet per minute. At this feed rate and speed of rotation, the solids within the kiln assumed a position between about 4 o'clock and six-thirty o'clock. The solids which reached the 4 o'clock position slid down gently to the lower level.

Under these conditions much of the inside walls of the kiln acquired a dusty film. When the knocker or thumper with which the kiln was equipped was activated, the film of dust over most of the length of the kiln disappeared and the bare metallic wall of the kiln could be seen. A thin layer of solid formed on the inside wall starting about one foot from the point where the kiln entered the shroud and extending for eight (8) to twelve (12) inches. This deposit stayed at the same thickness throughout the entire test program. Just as dust could be seen dripping away from the kiln wall, dust could be seen dropping away from this thin layer of material upon impact of the thumper with the kiln.

In this test the reaction mixture was subjected to slow rotation as well as linear travel throughout the length of the kiln. Since the solids traveled about eleven (11) feet in sixty minutes, the horizontal speed was about five and one-half (5½) feet per minute.

After about two hours it became apparent that a steady state condition had been reached and such an operation could be carried out continuously.

The product leaving the kiln was darker in color than the powdered feed and was decidedly granular. This showed some melting had taken place and that the melted phase had caused some of the adjoining powder to agglomerate. Analysis of the product showed that the final product contained only 0.9% aniline hydrogen sulfate. The original sulfanilic acid contained 4.2% metanilic acid. The product leaving the kiln contained 3.5% metanilic acid. This is the normal for the isomerization of metanilic acid to sulfanilic acid as the metanilic acid is heated above the rearrangement temperature.

Although the feed was in the kiln for an hour, much of this time it was below the rearrangement temperature.

As experience with the equipment was gained, the concentration of aniline hydrogen sulfate was increased and the feed rate decreased in order that there would be an increased amount of liquid phase in the reacting mixture at some point during its residence within the kiln. In addition, the temperature within the shroud was increased to a maximum of about 280° C.

Steady state operation was obtained when the initial feed contained both 10% aniline hydrogen sulfate and 16% aniline hydrogen sulfate. The feed rates were 10 pounds per hour. The total of sulfanilic acid and metanilic acid was in excess of 95%. The metanilic acid concentration was about 1%. These results were achieved with the feed subjected to relatively high conversion temperatures for only about thirty (30) minutes.

At higher aniline hydrogen sulfate feed concentrations, the product leaving the kiln had a larger particle size. This resulted from the presence of an increased percentage of liquid phase in the reaction mixture during the rearrangement.

Although the feed was powdered, some of the product was larger than six (6) mesh (U.S., Sieve Series). A portion of the product was screened. The plus six (6) mesh material was crushed and a sample analyzed. The aniline hydrogen sulfate content was less than 1.4%.

EXAMPLE 3

Although it was known that the reaction forming aniline hydrogen sulfate was exothermic, the actual amount of heat liberated in the reaction was not known. To obtain a measure of the heat of reaction, the reaction was carried out in an inert solvent in a bench scale calorimeter. It was found that the heat of reaction is close to 33 kilocalories per gram mole of aniline hydrogen sulfate formed. This is approximately 340 Btu per pound. By operating continuously, without intermediate cooling steps, this heat is theoretically almost enough to vaporize the water given off and supply the energy for the migration of the sulfonic acid group to the para position.

EXAMPLE 4

Using the information gained from the heat-of-reaction data obtained in Example 3 and the moving-bed observations of Examples 1 and 2, an industrial scale, sulfanilic acid unit was designed according to the illustration in the Drawing consisting of FIGS. 1 and 2. FIG. 1 shows a plan view from above, parts cutaway, of the designed sulfanilic acid production unit 1. FIG. 2 is a similar side elevation of the unit.

The feeds of aniline and concentrated sulfuric acid are fed to the production unit 1 from stainless steel tanks (not shown) via aniline pipe 2 and sulfuric acid pipe 3. Cannister 4 filled with granulated carbon is connected to the vent opening in the aniline tank (not shown). Cannister 4 prevents aniline fumes from venting to the atmosphere when the aniline feed tank is being filled.

Metering pumps 5 and 6, astride pipes 2 and 3 for the aniline and sulfuric acid, individually pressurize and control rates of respective addition of these reactants.

Static mixer 7 terminating pipe 2 is used to mix the fresh aniline with the recycled aniline recovered as aniline hydrogen sulfate as described below and fed by metering pump 8 to mixer 7. The combined anilines are led from mixer to the reactor by pipe 9.

In the version of the process of this example, the aniline and sulfuric acid are mixed and reacted before introduction into the cascading bed consisting of sulfanilic acid particles.

The reactor 10 containing cascading bed 11 is a divided stainless steel rotating cylindrical reactor comprising a feed section 12 separated from completion section 13 by a partition 14.

Partition 14 is provided with an opening 15 whose area is comparable to the inlet and outlet areas to provide control of the transfer rate of the cascading particulate bed 11 between the feed section 12 and completion section 13. Contained in completion section 13 and admixed with the portion of the cascading bed 11 therein are stainless steel balls 16 which act as grinding media for the cascading contents of bed 11. The feed section 12 of reactor 10 is provided with flights for agitating and advancing bed 11 toward opening 15 in partition 14 and into completion section 13.

The combined aniline feeds from static mixer 7 is fed as the first fluid via pipe 9 to a two-fluid mixer nozzle 20. Sulfuric acid from pump 6 via pipe 3 is fed as the second fluid to the two-fluid mixing nozzle 20. Nozzle 20 is positioned at the beginning of the feed section 12 of reactor 10 and above fluidized bed 11. The spray 21 from nozzle 20 is directed so that the reacted and combined molten liquid aniline hydrogen sulfate resulting from the contacting of the aniline and sulfuric acid in nozzle 20 and its spray 21 is introduced into the vortex resulting from the movement of cascading bed 11, consisting of sulfanilic acid particles by rotating reactor 10.

The reactor 10 is rotated on bearings 24 by means of motor 22 and gears 23. The long axis of reactor 10 is slightly depressed from the horizontal to facilitate progress of cascading bed 11 through reactor 10 toward product outlet 25.

Flights 17 are positioned in such a manner that when reactor 10 is revolving, the solids close to the initial portion of the feed section 12 are directed toward the partition 14. Flights close to the partition 14 are positioned to redirect most of the contents of bed 11 toward the middle of feed section 12. In this manner the incoming spray 21 of aniline hydrogen sulfate introduced into the fluidized bed 11 vortex is immediately commingled with the large amounts of the previously rearranged and formed particulate sulfanilic acid comprising the cascading bed 11.

Heat is supplied to reactor 10 and its cascading bed 11 contents by induction heating strip inductor 26. Induction heating current at the required frequency is supplied by a motor generator (not shown) to a water-cooled strip inductor 26. Strip inductor 26 is positioned beneath and along the bottom of the feed section 12 of reactor 10. The advantage of this heating method is that the maximum temperature within the system is at the portion of the reactor passing over, and when juxtaposed with inductor 26.

This provides excellent temperature control of the temperature of the fluidized bed 11 as when the induction current is reduced or cut there can be no further increase of the cascading bed particle temperature as there is no heated surface or mass at higher temperature to provide residual heat sink. This contrasts with the previously used furnaces which surrounded the reactor contents. Such masses continue to supply heat to the reaction mass by radiation or conduction even though the supply of fuel has been cut off.

As indicated above (Example 3), most of the heat needed to cause migration and rearrangement of the sulfanic acid group and to drive off water can be obtained by the properly conserved heat of reaction between the aniline and sulfuric acid. By causing this reaction adjacent to, and within the cascading bed 11 where the rearrangment takes place, little additional heat input is needed once the temperature of the bed 11 is above about 180° C. Heat input is only required to offset thermal losses from the reactor and to bring the temperature of the bed 11 to the operating level, about 160° C. and to the preferred operating level at about 180° C. It is preferred to initiate the feed of reactants, aniline and sulfuric acid, when the bed reaches the preferred temperature.

Because of the substantial amounts of heat furnished by the initial aniline-sulfuric acid reaction, the heating capacity of the induction heating system is determined by balancing the length of start-up time against the capital investment for the heating system. A unit, as described herein, producing 300 pounds per hour of sulfanilic acid, employing a reactor residence time of about 6 hours, requires a motor generator of about 50 KVA capacity if the start up time is to be kept below about 6 hours and 40% less if a 20 hour start up time is affordable.

When aniline hydrogen sulfate is heated above the rearrangement temperature, water vapor is given off along with a small amount of aniline vapor. To prevent the toxic aniline vapor from reaching the atmosphere, the vapor leaving the reactor 10 from atop opening 28 in the feed breeching is passed through a scrubber consisting of a venturi contactor 30 and liquid-gas separator 29. The upper outlet 32 of the separator is connected to an outlet stack 33. The lower outlet of the separator 29 is connected to sump 35. Pump 36 recirculates the scrub solution which is maintained slightly acid by the controlled addition of sulfuric acid. The acid in solution removes the aniline while allowing the water vapor to escape through stack 33. The scrub solution is continuously recycled. Its pH is maintained close to 2. To insure the flow of water and aniline vapor from the reactor to the scrubber and out of the stack, a fan, not shown, is installed, at the top of the stack. Air leakage from product outlet and air inlet 25 is induced in this way. As operation continues, the concentration of aniline hydrogen sulfate in the scrub solution builds up. A small amount of the recycled, concentrated aniline sulfate solution is bled from the scrubbing circuit 34 and mixed with the aniline in the static mixer 7 via pump 8 and the combined mixture fed to the two-fluid nozzle 20 as described above.

Flights are attached to the inside surface of the reactor. They are positioned in such a manner that when the reactor is revolving, solids close to the feed end are picked up and directed towards the middle of the reactor. The flights attached to the reactor close to the partition separating the feed section (8) of the reactor from the outlet section (9) are positioned so that solids are picked up and also directed towards the middle section. By this means the incoming aniline hydrogen sulfate is immediately commingled with a large amount of previously formed sulfanilic acid.

The operating procedure is as follows:

The feed section 12 of the reactor is filled to the bed operating level 11 with performed, powdered sulfanilic acid. Power is fed to the motor 22 which turns the reactor via gears 23. When the reactor is moving so that the bed is in its operating mode, power is fed to the inductor 26. As soon as the temperature in the bed approaches about 180° C., circulation of the scrub solution in scrubber circuit 29 starts and the fan in stack 33 is turned on. A small controlled amount of water from the scrub solution is fed to the mixing nozzle 20 and then aniline and sulfuric acid in mole to mole proportions by pumps 5 and 6 are fed to the system. To minimize the escape of toxic aniline vapor from the reactor, a slight excess of sulfuric acid is always fed to the process. As soon as the flow of aniline and sulfuric acid is established, the flow of water is gradually diminished. In this way there is no likelihood that aniline hydrogen sulfate will form and solidify inside the nozzle while it is cold. The heat of reaction will heat the nozzle above 160° C., the melting point of aniline hydrogen sulfate. The temperature of the moving bed is monitored. Power to the inductor 26 is controlled so that the bed's temperature remains between about 180° C. and 200° C.

As the feed continues, the level of solids in the feed section increases to the point where it overflows into the completion section 13 of the reactor 10. The outlet section serves several purposes. It affords additional residence time to complete the reaction and eliminate any substantial incompletion of the rearrangement from occurring. Agglomerates are broken into smaller particles. This insures that any unreacted aniline hydrogen sulfate will be subjected to the rearrangement temperature since the small particle size insures that it will not be insulated by a layer of sulfanilic acid while still in the reactor. The final product proceeds from the completion section 13 to the combined product outlet and air inlet 25. The product is channeled into suitable storage containers via conveyers (not shown).

EXAMPLE 5

The same equipment arrangement of Example 4 can be used, but two small changes, when forming the aniline hydrogen sulfate within the bed or immediately before liquid aniline hydrogen sulfate coats the particles within the turbulent rolling vortex of the bed. To form the aniline hydrogen sulfate within the bed, two spray nozzles are employed to replace nozzle 20 of Example 4. They are positioned so that the spray from each intersect and intermingle. It is also desirable to have the sprays in close proximity to each other as well as be within the falling curtain of solid particles formed when the particles drop from the flights 17 which elevate them. This arrangement insures that all of the heat of reaction evolved when aniline hydrogen sulfate forms is available for dehydration and the rearrangement conversion to sulfanilic acid.

As we pointed out above, this invention is applicable to the economic production of many different sulfonated aromatic amines. In the above examples, the production of sulfanilic acid was described in detail. The same procedures can be used to make other sulfonated aromatic amines. The required differences are the use of appropriate components and rearrangement temperatures. Such rearrangement temperatures are well known. Table 1 below contains this requisite information. In each instance the amine listed is reacted with slightly more than the stoichiometric amount of sulfuric acid to form the corresponding sulfate salt using the same procedures described above. The salt at its elevated temperature or its components are added to the cascading bed of particles of indicated final product which is maintained above the minimum rearrangement temperature but below the decomposition temperature. The use of the final product as the rearrangement bed appears to substantially promote proper rearrangement.

TABLE 1

| Starting Material | Rearrangement Temperature 175° C. | Product |
|---|---|---|
| aniline ($NH_2$) | | 4-aminobenzenesulfonic acid ($NH_2$, $SO_3H$ para) |
| 2-methylaniline ($CH_3$, $NH_2$ ortho) | 235 | ($CH_3$, $NH_2$, $HO_3S$) |
| 3-methylaniline ($CH_3$, $NH_2$ meta) | 255 | ($CH_3$, $NH_2$, $HO_3S$) |
| 4-methylaniline ($CH_3$ para to $NH_2$) | 160 | ($CH_3$, $NH_2$, $SO_3H$) |
| 2-chloroaniline ($NH_2$, $Cl$) | 230 | ($NH_2$, $SO_3H$, $Cl$) |
| 2-ethoxyaniline ($OC_2H_5$, $NH_2$) | 175 | ($OC_2H_5$, $NH_2$, $SO_3H$) |

What is claimed is:

1. In the method for the production of sulfonated aromatic amines of the formula:

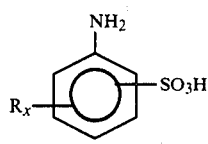

where R is H, CH$_3$, C$_2$H$_5$, or halogen; and x is the integer 0 to 2; wherein the aromatic amine of the formula

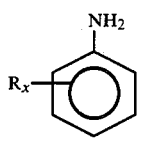

is treated with concentrated sulfuric acid to form the aromatic amine sulfate at the amine group of the formula

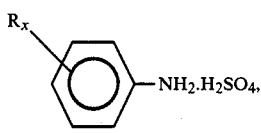

which is then heated to eliminate a mole of water with a rearrangement of the thus formed sulfonate group to the position para or ortho to the restored amine group; the improvement which comprises continuously adding the aromatic amine and concentrated sulfuric acid reactants and mixtures thereof unto and into an indirectly heated, rolling, cascading bed of the preformed, desired, sulfonated, aromatic amine, said bed being maintained above the rearrangement temperature for said sulfonated amine, to eliminate the water from the amine sulfate and to direct the rearrangement of the dehydrated sulfate to the desired sulfonate orientation by the crystalline matrix of the final product comprising said cascading bed and continuously withdrawing the desired sulfonated amine.

2. In the process according to claim 1 wherein the aromatic amine sulfonate is sulfanilic acid of the formula

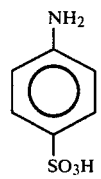

formed when aniline is treated with concentrated sulfuric acid to form the intermediate aniline acid sulfate and wherein said improvement comprises introducing the aniline and sulfuric acid components and mixtures thereof into and unto a rolling vortex formed in a heated rapidly moving, cascading bed of sulfanilic acid particles contained in a reactor rotating on a horizontal axis, said bed being heated to above 160° C. to eliminate water from and to rearrange the intermediate to said sulfanilic acid.

3. The process according to claim 2 wherein the vortex of cascading, in rapidly moving bed of sulfanilic acid particles is formed by having said bed of sulfanilic acid particles contained in a rotating, substantially, horizontally disposed, generally cylindrical, tubular reactor equipped with means for advancing the bed material from the initial end to the distal end, said reactor including a liquid-spray, feed system wherein sulfuric acid and aniline and mixtures thereof at said initial end are directed into and under the vortex created by said cascading of the bed, for intimate contact of said sprayed feed with said heated bed of sulfanilic acid.

4. The process according to claim 3 wherein said reactor is fitted with spray means at its initial portions for introduction of said aniline and sulfuric acid onto and within the vortex of said cascading bed of sulfanilic acid particles formed by rotation of said reactor.

5. The process according to claim 4 wherein said aniline and sulfuric acid are simultaneously sprayed below the surface of said cascading vortex bed.

6. The process according to claim 4 wherein aniline and sulfuric acid are premixed, reacted and sprayed into said vortex.

7. The process according to claim 3 wherein said cascading bed is primarily heated to above 160° C. by the reaction of said heat being supplied by external application through portions of said reactor to said cascading bed of sulfanilic acid.

8. The process according to claim 7 wherein said balance of heat is supplied to the reactor portions by an appropriately positioned external furnace.

9. The process according to claim 7 wherein said balance of heat is supplied by a juxtaposed electrical induction heating source.

10. The process according to claim 7 wherein said bed is heated to the temperature range of 180° C.–200° C.

* * * * *